(12) United States Patent
Cao et al.

(10) Patent No.: US 12,324,920 B2
(45) Date of Patent: Jun. 10, 2025

(54) IMPLANTABLE MEDICAL DEVICE WITH PACING CAPTURE CLASSIFICATION

(71) Applicant: Medtronic, Inc., Minneapolis, MN (US)

(72) Inventors: Jian Cao, Shoreview, MN (US); Elizabeth A. Mattson, Eagan, MN (US); Todd J. Sheldon, North Oaks, MN (US); Xiaohong Zhou, Woodbury, MN (US); Wade M. Demmer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/401,185

(22) Filed: Aug. 12, 2021

(65) Prior Publication Data

US 2022/0062645 A1    Mar. 3, 2022

Related U.S. Application Data

(60) Provisional application No. 63/072,685, filed on Aug. 31, 2020.

(51) Int. Cl.
*A61N 1/37*  (2006.01)
(52) U.S. Cl.
CPC .................................. *A61N 1/3712* (2013.01)
(58) Field of Classification Search
CPC ...... A61N 1/3712; A61B 5/4836; A61B 5/29; A61B 5/397; A61B 5/7267; A61B 5/395
See application file for complete search history.

(56) References Cited

U.S. PATENT DOCUMENTS

| 5,871,507 A | * | 2/1999 | Obel | A61N 1/3704 607/9 |
|---|---|---|---|---|
| 6,192,273 B1 | | 2/2001 | Igel et al. | |
| 7,751,873 B2 | | 7/2010 | de Voir | |

(Continued)

FOREIGN PATENT DOCUMENTS

WO    2019089510 A1    5/2019

OTHER PUBLICATIONS

Saini et al., "Novel Method for Assessment of His Bundle Pacing Morphology Using Near Field and Far Field Device Electrograms", Circulation: Arrhythmia and Electrophysiology, Feb. 2019, 11 pp.

(Continued)

*Primary Examiner* — Ankit D Tejani
*Assistant Examiner* — Joshua Brendon Solomon
(74) *Attorney, Agent, or Firm* — Shumaker & Sieffert, P.A.

(57) ABSTRACT

This disclosure is directed to devices and techniques for classifying of pacing captures to evaluate effectiveness of pacing by a pacing device, such as an implantable medical device (IMD). An example system includes stimulation circuitry to generate a pacing stimulus, sensing circuitry to sense an evoked response after the pacing stimulus, and processing circuitry. The processing circuitry determines classification features from the evoked response and applies the classification features to a classification model, the classification model generated by a machine learning algorithm using one or more test sets comprising a plurality of sample evoked responses for each of a plurality of classifications. Based on the output of the model, the processing circuitry classifies the evoke response as one of the plurality of classifications.

19 Claims, 8 Drawing Sheets

(56) References Cited

U.S. PATENT DOCUMENTS

| | | | |
|---|---|---|---|
| 8,750,999 B1 | 6/2014 | Ghosh et al. | |
| 8,831,726 B2 | 9/2014 | Kim et al. | |
| 9,002,454 B2 | 4/2015 | Ghosh et al. | |
| 9,308,375 B2 | 4/2016 | Kim et al. | |
| 9,415,227 B2 | 8/2016 | Betzold | |
| 9,993,205 B2* | 6/2018 | Meyer | A61B 5/7264 |
| 10,413,203 B2 | 9/2019 | Saha et al. | |
| 10,448,853 B2* | 10/2019 | Mahajan | G16H 50/70 |
| 10,881,862 B2 | 1/2021 | Ghosh | |
| 11,007,369 B2 | 5/2021 | Sheldon et al. | |
| 11,027,136 B2 | 6/2021 | Mangual-Soto et al. | |
| 2010/0318148 A1* | 12/2010 | Bornzin | A61N 1/3627 607/17 |
| 2012/0101543 A1* | 4/2012 | Demmer | A61N 1/3712 607/28 |
| 2013/0018433 A1* | 1/2013 | Shome | A61N 1/3712 607/28 |
| 2014/0163633 A1 | 6/2014 | Ghosh et al. | |
| 2014/0243690 A1 | 8/2014 | Dumont et al. | |
| 2016/0114169 A1* | 4/2016 | Sheldon | A61N 1/365 607/17 |
| 2019/0046113 A1* | 2/2019 | Nikolic | G06F 18/24133 |
| 2019/0083800 A1 | 3/2019 | Yang et al. | |
| 2019/0126050 A1 | 5/2019 | Shuros et al. | |
| 2019/0134404 A1* | 5/2019 | Sheldon | A61N 1/3956 |
| 2019/0232065 A1 | 8/2019 | Perschbacher et al. | |
| 2020/0094058 A1* | 3/2020 | Mangual-Soto | A61N 1/056 |
| 2020/0254248 A1* | 8/2020 | Atwater | A61N 1/39622 |
| 2020/0406041 A1* | 12/2020 | Cao | G16H 50/20 |
| 2021/0016097 A1* | 1/2021 | Mangual-Soto | A61N 1/3712 |

OTHER PUBLICATIONS

International Search Report and Written Opinion of International Application No. PCT/US2021/046798, dated Nov. 18, 2021, 8 pp.

* cited by examiner

IMPLANTABLE MEDICAL DEVICE WITH PACING CAPTURE CLASSIFICATION

RELATED APPLICATION

This application claims the benefit of U.S. Provisional Application No. 63/072,685, filed Aug. 31, 2020, the entire contents of which is incorporated herein by reference.

TECHNICAL FIELD

This disclosure generally relates to medical devices, and more specifically, delivery of cardiac pacing by medical devices.

BACKGROUND

Cardiac pacing is delivered to patients to treat a wide variety of cardiac dysfunctions. Cardiac pacing is often delivered by an implantable medical device (IMD). An implantable cardioverter-defibrillator (ICD), for example, may provide pacing functionality and also provide cardioversion or defibrillation in response to detected cardiac tachyarrhythmias, if needed. An IMD typically delivers such therapy to the heart via electrodes located on one or more leads, which may be intracardiac or extracardiovascular leads, although leadless IMDs for delivering such therapies have also been implemented. Patients with heart failure may be treated with cardiac resynchronization therapy (CRT). CRT is a form of cardiac pacing. The ventricles of some heart failure patients contract in an uncoordinated, or asynchronous, manner, which greatly reduces the pumping efficiency of the ventricles. CRT delivers pacing pulses at particular times, e.g., atrioventricular (A-V) intervals and/or intra-ventricular (V-V) intervals, and particular locations, e.g., to one or both of the right and left ventricles, to re-coordinate the contraction of the ventricles. In some examples, CRT involves delivery of pacing pulses to both ventricles to synchronize their contraction. In other examples, CRT involves delivery of pacing pulses to one ventricle, such as the left ventricle, to synchronize its contraction with that of the right.

SUMMARY

In general, the disclosure is directed to devices and techniques for classifying of pacing captures to evaluate effectiveness of pacing by a pacing device, such as an implantable medical device (IMD). The techniques described here use the physiologically meaningful features of an evoked response to pacing to classify the capture of cardiac tissue by the pacing delivered by the pacing device. These features can be measured or derived from the sample evoked response.

Machine learning is used to produce a model that can be run on the relatively limited processing capacity of an IMD. Evoked responses may be categorized to reflect the effectiveness of pacing. For example, evoked responses may be categorized, in order of effectiveness, as "selective capture," "non-selective capture," "right ventricular (RV) capture," or "no ventricular capture." Samples of evoked responses are collected for each classification. In some examples, these sample evoked responses may include different measurements made by an implantable devices, such as, far field (FF) measurements, near field measurements (NF), and differential (DIFF) measurements. To prepare for model generation, the physiologically meaningful features are calculated and/or derived for each sample. These prepared samples are used to generate one or more training sets and one or more test sets. The training sets used to train a machine learning algorithm to classify pacing captures. Different machine algorithms may be used. For example, a classification algorithm or a regression algorithm may be used. In some examples, a classification machine learning algorithm may produce a decision tree to classify the pacing based on the features of the evoked response. The decision tree may, in some examples, identify key features from the physiologically meaningful features that are used to classify the pacing capture.

The model is downloaded to the IMD with the physiologically meaningful features that are used to classify the pacing. Periodically (e.g., hourly, daily, weekly, monthly, etc.), the IMD implements a pacing test to evaluate the current pacing settings and, when necessary, adjust the pacing settings. The pacing test provides pacing to the heart and the IMD captures the resulting evoked responses. IMD extracts the physiologically meaningful features from the evoked responses and implements the model to classify the pacing. Based on the classification, the implantable device may adjust, for example, the voltage level of the stimulation provided by an electrode of the IMD. For example, patient experience and/or device performance may be better when a relatively low voltage is used by the IMD while still providing "selective capture" pacing. In some examples, the voltage provided in the pacing stimulation may be adjusted during the pacing test to determine whether a lower voltage will still provide "selective capture" pacing. In this example, when a lower stimulation voltage can be used to provide effective therapy, the patient receives the therapy while the battery life of the IMD increases.

An example system includes stimulation circuitry configured to generate a pacing stimulus, sensing circuitry configured to sense an evoked response after the pacing stimulus, and processing circuitry. The processing circuitry is configured to determine classification features from the evoked response and apply the classification features to a classification model, the classification model generated by a machine learning algorithm using one or more test sets comprising a plurality of sample evoked responses for each of a plurality of classifications. Based on the output of the model, the processing circuitry is configured to classify the evoked response as one of the plurality of classifications.

An example method comprises generating a pacing stimulus and sensing an evoked response after the pacing stimulus. The method also includes determining classification features from the evoked response. The method also includes applying the classification features to a classification model. The classification model is generated by a machine learning algorithm using one or more test sets comprising a plurality of sample evoked responses for each of a plurality of classifications. Additionally, the method includes, based on the output of the model, classifying, by the processing circuitry, the evoke response as one of the plurality of classifications.

An example computer readable medium comprising instructions, that when executed, cause an implantable medical device (IMD) to generate, by stimulation circuitry, a pacing stimulus, and sense, by sensing circuitry, an evoked response after the pacing stimulus. The instructions also cause the IMD to determine, by processing circuitry, classification features from the evoked response, and apply the classification features to a classification model. The classification model is generated by a machine learning algorithm using one or more test sets comprising a plurality of sample evoked responses for each of a plurality of classifications. Further, the instructions cause the IMD to, based on the output of the model, classify, by the processing circuitry, the evoked response as one of the plurality of classifications.

The summary is intended to provide an overview of the subject matter described in this disclosure. It is not intended to provide an exclusive or exhaustive explanation of the systems, device, and methods descry bed in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
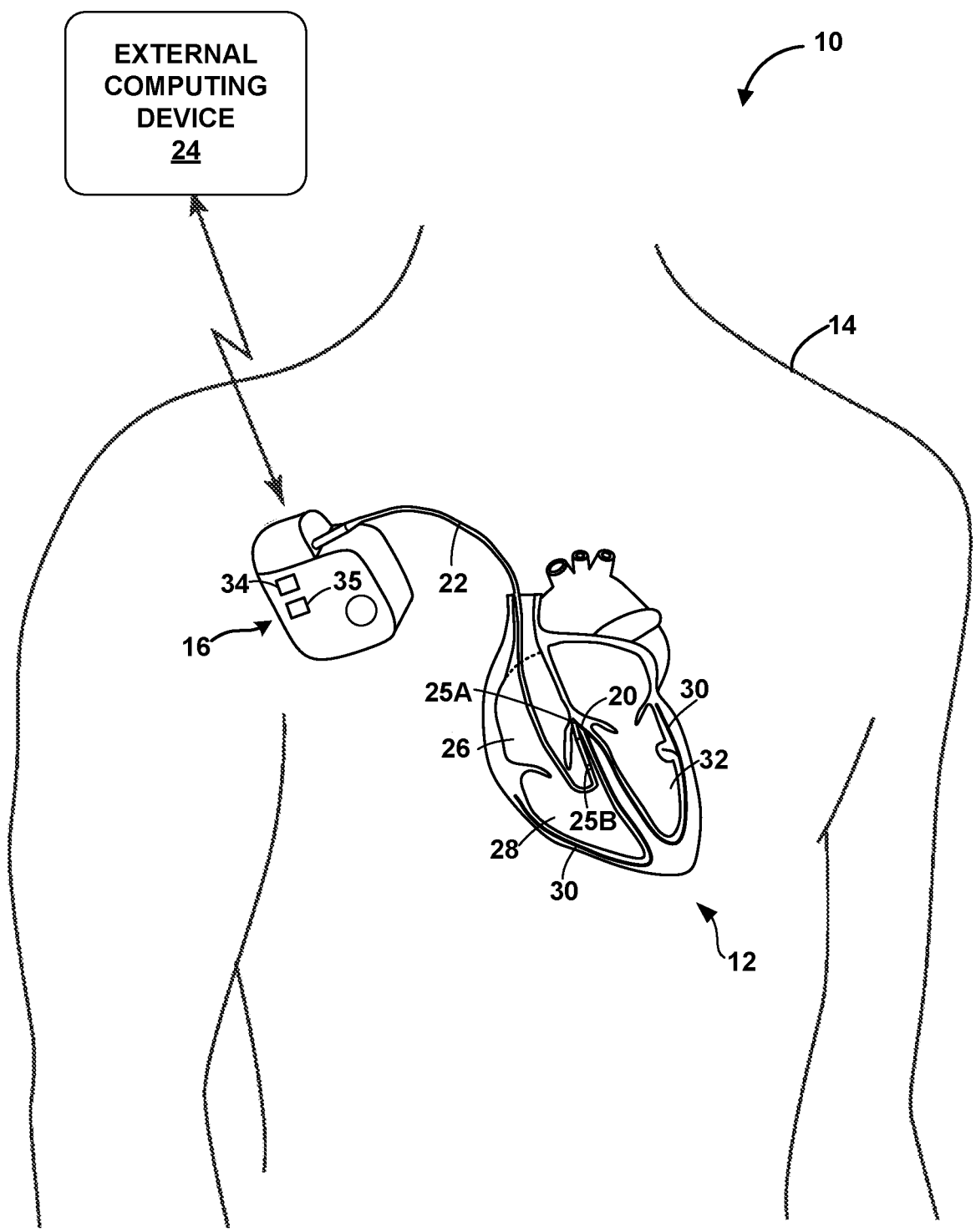
FIG. 1 is a conceptual diagram illustrating an example system for classifying evoked responses to determine an effectiveness of pacing, in accordance with the teachings of this disclosure.

This disclosure is directed to devices and techniques for classifying of pacing captures to evaluate effectiveness of pacing by a pacing device, such as an implantable medical device (IMD). As used herein, "pacing" refers to the delivery of an electrical impulse and "capture" refers to depolarization of myocardial cells by an electrical impulse. An IMD, such as a pacemaker, is connected to electrodes that are in contact with heart muscle. Pacing by the implantable device at the electrodes cause capture to occur in a wave across the heart muscle. Generally, this depolarization wave causes the heart to beat. From time to time, shortly after delivering the electrical stimulation (e.g., within 90 to 120 milliseconds, etc.), the IMD measures an evoked electrical response of the heart muscle. The morphology of the evoked response is indicative of which parts of the heart were affected by the pacing and in which sequence they were affected. This indicates the effectiveness of the pacing (sometimes referred to as "beat truthing").

The IMD may classify the response of the heart muscle to the pacing based on the characteristics of the evoked response to determine the effectiveness of the pacing. Pacing, as evidenced by the evoked response, can be classified into several categories. For example, for His bundle pacing (HBP), or other conduction system pacing, the pacing may be classified as "selective capture," "non-selective capture," "right ventricular (RV) capture," or "no ventricular capture." Generally, selective capture is preferable to non-selective capture (which is preferable to RV capture), while no ventricular capture is undesirable. Selective capture, for example, implies capture of the His bundle alone with resulting conduction via the His-Purkinje axis, leading to a QRS duration and morphology identical (or substantially identical) to the patient's native QRS duration. As another example, non-selective capture implies the additional capture of the septal myocardium, resulting in right ventricular (RV) myocardial pre-excitation and initial slurring and widening of the QRS complex. RV pacing implies excitation primarily of the RV myocardium and a widening of the QRS complex.

As described below, the IMD uses physiologically meaningful features of the evoked response to pacing to classify the pacing. These features can be measured or derived from the evoked responses. Machine learning is used to produce a model that can be run on the relatively limited processing capacity of an IMD. Additionally or alternatively, the model may run off-line or in a cloud. In some examples, the model may be optimized (e.g., the training set customized) based on a certain population (e.g., a shared location and/or a shared set of demographic and physical data, etc.) and/or individual patient data. The classification of the evoked responses may reflect the effectiveness of pacing. Samples of evoked responses are collected for each classification. In some examples, these sample evoked responses may include different measurements made by an implantable device, such as, far field (FF) measurements, near field measurements (NF), and differential (DFF) measurements. To prepared for model generation, the physiologically meaningful features are calculated and/or derived for each sample. These prepared samples are used to generate one or more training sets and one or more test sets. The training sets used to train a machine learning algorithm to classify pacing captures. Different machine algorithms may be used, such as a classification algorithm or a regression algorithm, or an ensemble learning method for classification and regression (e.g., random forests or random decision forests). In some examples, a classification machine learning algorithm may produce a decision tree model to classify the pacing based on the features of the evoked response. The decision tree may, in some examples, identify key features from the physiologically meaningful features that are used to classify the pacing.

The model is downloaded to the IMD with the physiologically meaningful features that are used to classify the pacing. Periodically (e.g., daily, weekly, monthly, etc.), the IMD implements a pacing test to evaluate the current pacing settings and, when necessary, adjust the pacing settings. The pacing test provides pacing to the heart and IMD captures the resulting evoked responses. IMD extracts the physiologically meaningful features from the evoked responses and implements the model to classify the pacing. Based on the classification, the implantable device may adjust, for example, the voltage level of the stimulation provided by an electrode of the IMD. For example, patient experience may be better when a relatively low voltage is used by the IMD while still providing "selective capture" pacing. In some examples, the voltage provided in the pacing stimulation may be adjusted during the pacing test to determine whether a lower voltage will still provide "selective capture" pacing. In this example, when a lower stimulation voltage can be used to provide effective therapy, the patient receives the therapy while the battery life of the IMD increases.

FIG. 1 is a conceptual diagram illustrating an example system 10 for classifying evoked responses to determine an effectiveness of pacing. As illustrated by example system 10 in FIG. 1, a system for classifying evoked responses according to the techniques of this disclosure may include an implantable medical device (IMD) 16 with pacing capabilities. IMD 16 is connected to lead 22 and is communicatively coupled to external device 24. IMD 16 senses electrical signals attendant to the depolarization and repolarization of heart 12, e.g., an EGM, via electrodes on one or more of lead 22 and/or the housing of IMD 16. IMD 16 may also deliver therapy in the form of electrical signals to heart 12 via electrodes located on lead 22. The therapy may be pacing, cardioversion and/or defibrillation pulses. IMD 16 may monitor EGM signals collected by electrodes on lead 22, and based on the EGM signal, classify the pacing to determine its quality.

Lead 22 (sometime referred to as a "His bundle lead") extends into heart 12 of patient 14 to sense electrical activity of heart 12 and/or deliver electrical stimulation to heart 12. In the example shown in FIG. 1, lead 22 extends through one or more veins (not shown), the superior vena cava (not shown), and right atrium 26, and into right ventricle 28. IMD 16 may include additional leads, such as a left ventricular (LV) that extends through one or more veins, the vena cava, right atrium 26, and into the coronary sinus to a region adjacent to the free wall of left ventricle 32 of heart 12. Lead 22 is positioned to provide pacing to the His bundle 20 (providing pacing at this location is sometimes referred to as "His bundle pacing" or "HBP"). In the illustrated example, lead 22 is positioned to provide pacing to the His bundle 20 between an atrioventricular node (not shown) and branches of Purkinje fibers 30.

Quality and, in some examples, effectiveness of pacing may be determined by the reaction of heart 12 to pacing. His bundle 20 efficiently transmits impulses from the atrioventricular node of heart 12 to the ventricles (e.g., right ventricle 28 and left ventricle 32) of heart 12 via Purkinje fibers 30. The depolarization of myocardial cells caused by HBP may resemble the depolarization of myocardial cells caused by natural pacing. The capture resulting from pacing that primarily affects His bundle 20 is referred to as "selective capture." In some examples, pacing may cause additional capture of the septal myocardium that results in right ventricular (RV) myocardial pre-excitation (e.g., stimulus affects His bundle 20 and additional septal myocardium, etc.). The resulting capture may be referred to as "non-selective capture." Capture that is primarily of the septal myocardium of the right ventricle may be referred to as "RV capture." Pacing that does not affect the His bundle or the septal myocardium of the right ventricle may be said to have caused "no ventricular capture."

In some examples, external device 24 takes the form of a handheld computing device, computer workstation or networked computing device that includes a user interface for presenting information to and receiving input from a user. A user, such as a physician, technician, surgeon, electrophysiologist, or other clinician, may interact with external device 24 to retrieve physiological or diagnostic information from IMD 16. A user may also interact with external device 24 to program IMD 16, e.g., select values for operational parameters of the IMD. External device 24 may include processing circuitry configured to evaluate EGM signals transmitted from IMD 16 to external device 24.

IMD 16 and external device 24 may communicate via wireless communication using any techniques known in the art. Examples of communication techniques may include, for example, low frequency or radiofrequency (RF) telemetry, or according to the Bluetooth® or Bluetooth LE specifications. In some examples, external device 24 may be located remotely from IMD 16 and communicate with IMD 16 via a network.

System 10 of FIG. 1 is an example of a system for classifying evoked responses resulting from pacing to determine an effectiveness and/or quality of pacing. Processing circuitry of IMD 16 includes pacing analysis circuitry 34 and classification model 35 configured to classifying evoked responses resulting from pacing. From time to time, shortly after delivering the electrical stimulation (e.g., within 90 to 120 milliseconds, etc.), the cardiac signal analysis circuitry measures an evoked electrical response (sometimes referred to as an "evoked response") characterizing the depolarization wave of the heart muscle of heart 12. The evoked response is measured via a cardiac electromyogram (EGM) sensed via one or more electrodes of IMD 16. The cardiac signal analysis circuitry may measure far field (FF) potential (e.g., from RVtip electrode 25A of lead 22 to the exterior of IMD 16) and near field (NF) potentials (e.g., RVtip electrode 25A to RVring electrode 25B of lead 22). The cardiac signal analysis circuitry may also determine differential far field (DFF) potential (e.g., a first order differential of the FF potential, etc.). For example, a cardiac EGM that includes an evoked response may include P-waves (depolarization of the atria), R-waves (depolarization of the ventricles), and T-waves (repolarization of the ventricles), among other events. As described below, the cardiac EGM of an evoked response may include physiologically meaningful features. These physiologically meaningful features are extracted by pacing analysis circuitry 34. Pacing analysis circuitry 34 then uses classification model 35 to classify the evoked response. In some examples, IMD 16 may take actions based on the classification of the evoked response, such as adjusting pacing parameters and/or providing an alert (e.g., to external device 24).

Although the techniques for classifying evoked responses resulting from pacing to determine an effectiveness and/or quality of pacing according to the techniques of this disclosure are described herein primarily with reference to example system 10, the techniques may be performed by other systems that differ from example system 10. For example, systems for identifying the one or more parameters according to the techniques of this disclosure may include an IMD having different functionality than IMD 16, and may include more, fewer, or different implantable cardiac leads than lead 22. In some examples, systems for identifying the one or more parameters include more or fewer leads, do not include any intracardiac leads, or do not include any leads. Example IMDs that may implement the techniques of this disclosure in addition to the illustrated example of IMD 16 include intravascular or extracardiovascular ICDs, and transcatheter pacing systems, such as the Micra™ transcatheter pacing system commercially available from Medtronic plc, of Dublin, Ireland.

Figure 2:
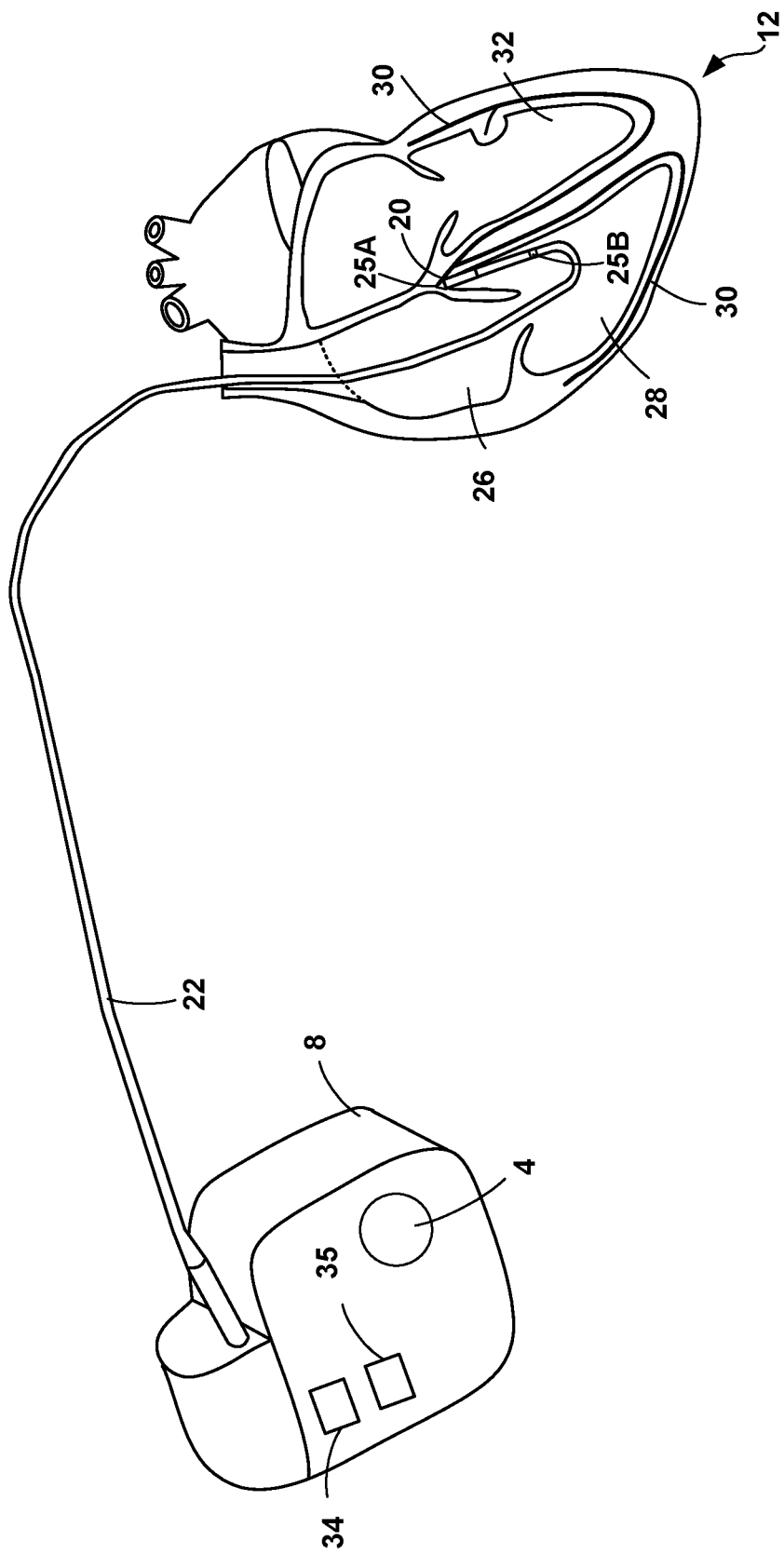
FIG. 2 is a conceptual diagram illustrating the IMD and leads of the system of FIG. 1 in greater detail.

FIG. 2 is a conceptual diagram illustrating IMD 16 and lead 22 of system 10 in greater detail. In the illustrated example, bipolar electrodes 25A is located adjacent to a distal end of lead 22. In the illustrated example, electrode 25A may take the form of extendable helix or tine tip electrodes. Electrode 25B may take the form of a ring electrode electrically insulated from tip electrode 25A. In some examples, each of electrodes 25A and 25B is electrically coupled to a respective conductor within the lead body of lead 22 and thereby coupled to circuitry within IMD 16.

In some examples, IMD 16 includes one or more housing electrodes, such as housing electrode 4 illustrated in FIG. 2, which may be formed integrally with an outer surface of hermetically sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode includes substantially all of housing 8.

Housing 8 encloses signal generation circuitry that generates therapeutic stimulation, such as cardiac pacing, cardioversion, and defibrillation pulses, as well as sensing circuitry for sensing electrical signals attendant to the depolarization and repolarization of heart 12. As described below, housing 8 may also enclose processing circuitry and memory configured with pacing analysis circuitry 34 and classification model 35. Housing 8 may also enclose telemetry circuitry for communication between IMD 16 and external device 24.

IMD 16 senses electrical signals attendant to the depolarization and repolarization of heart 12 via electrodes 4, 25A, and 25B. Any of the electrodes 25A and 25B may be used for unipolar sensing in combination with housing electrode 4. The illustrated numbers and configurations of lead 22 and electrodes 25A and 25B are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intracardiac lead 22, system 10 may include one or more extracardiovascular (e.g., epicardial, substernal, or subcutaneous) leads not positioned within the heart.

Figure 3:
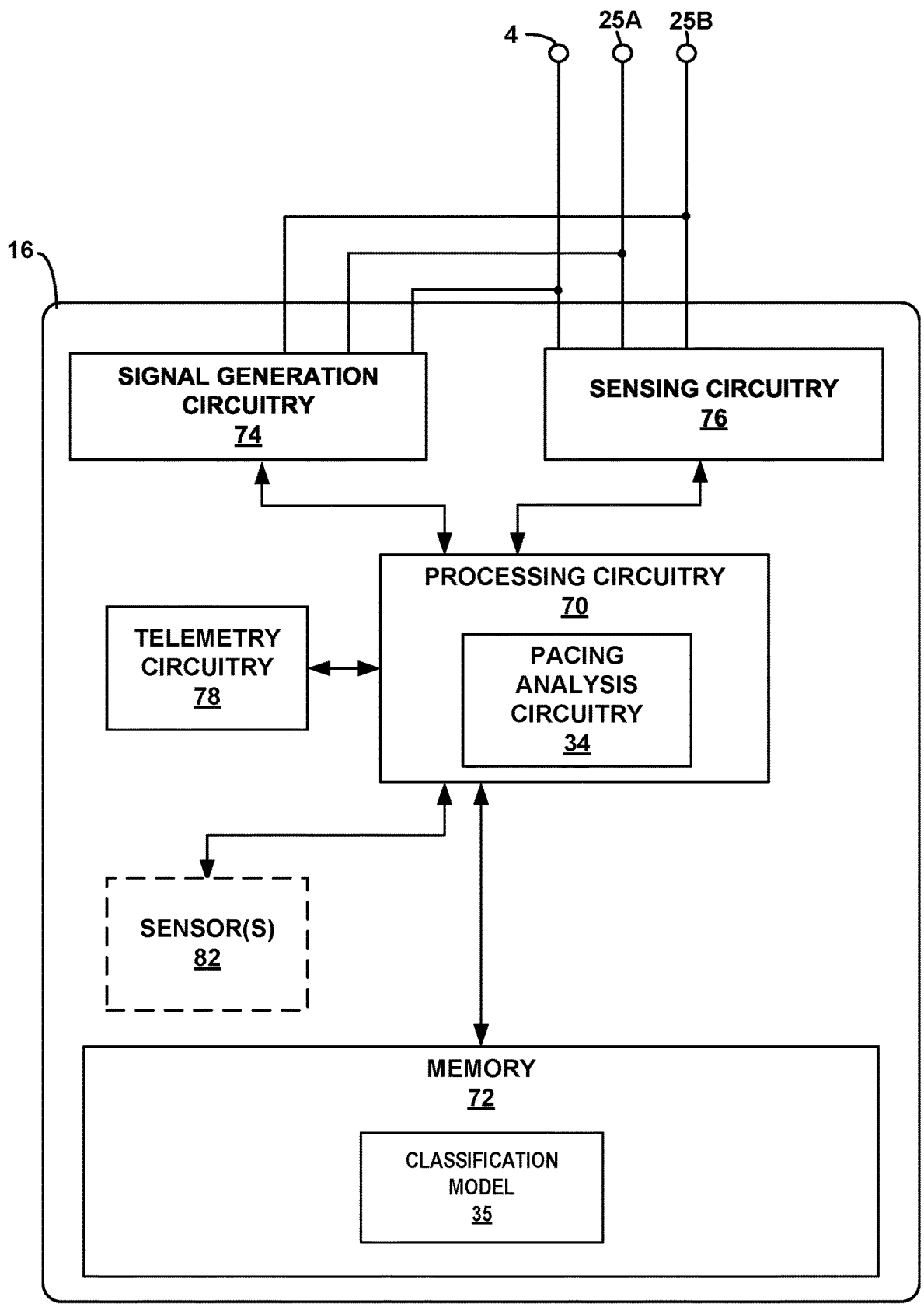
FIG. 3 is a block diagram illustrating an example configuration of an IMD for classifying evoked responses to determine an effectiveness of pacing, in accordance with the teachings of this disclosure.

FIG. 3 is a block diagram illustrating an example configuration of IMD 16. In the illustrated example, IMD 16 includes processing circuitry 70, memory 72, signal generation circuitry 74, sensing circuitry 76, telemetry circuitry 78, pacing analysis circuitry 34, and activity sensor 82. Memory 72 includes computer-readable instructions that, when executed by processing circuitry 70, cause IMD 16 and processing circuitry 70 to perform various functions attributed to IMD 16 and processing circuitry 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 70 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 70 may include multiple components, such as any combination of one or more microprocessors, one or more controllers, one or more DSPs, one or more ASICs, or one or more FPGAs, as well as other discrete or integrated logic circuitry. The functions attributed to processing circuitry 70 herein may be embodied as software, firmware, hardware, or any combination thereof.

Signal generation circuitry 74 is configured to generate and deliver pacing stimulation to patient 14. As shown in FIG. 3, signal generation circuitry 74 is electrically coupled to electrodes 4, 25A, and 25B, e.g., via conductors of lead 22 and, in the case of housing electrode 4, within housing 8. For example, signal generation circuitry 74 may deliver pacing, defibrillation, or cardioversion pulses to heart 12 via at least electrode 25A. In some examples, signal generation circuitry 74 delivers therapy in the form of signals other than pulses such as sine waves, square waves, or other substantially continuous time signals.

Electrical sensing circuitry 76 monitors electrical cardiac signals from any combination of electrodes 4, 25A, and 25B. Sensing circuitry 76 may also include switching circuitry which processing circuitry 70 controls to select which of the available electrodes are used to sense the heart activity, depending upon which electrode combination is used in the current sensing configuration. In some examples, sensing circuitry 76 may include one or more amplifiers, filters, and analog-to-digital converters.

Sensing circuitry 76 may include one or more detection channels, each of which may include an amplifier. The detection channels may be used to sense cardiac signals, such as cardiac EGMs indicative of an evoked response after signal generation circuitry 74 generates the pacing stimulation. For example, sensing circuitry 76 may sense an EGM of the NF potential and an EGM of the FF potential. Sensing circuitry 76 may apply a low-pass filter (e.g., 12 Hertz (Hz) at a 256 Hz sampling rate, etc.) and/or a five-point differential (e.g., at a 256 Hz sampling rate, etc.). The detection channels may provide the signals to an analog-to-digital converter, for conversion into a digital signal for processing or analysis by processing circuitry 70 or pacing analysis circuitry 34.

Periodically (e.g., daily, weekly, monthly, etc.), processing circuitry 70 may perform a series of test pacing to evaluate the pacing being provided to heart 12. During these series of test pacing, pacing analysis circuitry 34 causes sensing circuitry 76 to capture cardiac EGMs after signal generation circuitry 74 generates the pacing stimulation for the pacing tests. Pacing analysis circuitry 34 generates a DFF potential. Pacing analysis circuitry 34 extracts portions of the cardiac EGMs of the FF potential, the DFF potential, and/or the NF potential from a time period (e.g., 220 millisecond, etc.) after each pacing test stimulation. The portions extracted from the cardiac EMGs of the FF potential, the DFF potential, and/or the NF potential may be collectively referred to as the "evoked response" of that test pacing stimulation. For each evoked response, pacing analysis circuitry 34 extracts and/or derives physiologically significant features from the evoked response. Pacing analysis circuitry 34 uses classification model 35 to classify each evoked response based on these physiologically significant features. For example, pacing analysis circuitry 34 may classify each evoked response as "selective capture," "non-selective capture," "RV capture," or "no capture." In some examples, pacing analysis circuitry 34 may additionally or alternatively classify evoked responses to pacing other than the test pacing. For example, pacing analysis circuitry 34 may randomly or pseudo-randomly sample evoke responses after pacing for later analysis via, for example, external device 24. In some examples, processing circuitry 70 acts in response to the classification of the test pacing. For example, processing circuitry 70 may adjust stimulation voltage for pacing. In one scenario, processing circuitry 70 may reduce stimulation voltage during each subsequent test pacing until the stimulation voltage no longer provides selective capture.

Processing circuitry 70 may set the stimulation voltage to be the last voltage that provided selective capture plus, in some examples, an additional voltage margin.

Classification model 35 is a model that takes, as input, the physiologically significant features (sometimes referred to as the "classification features") and outputs the classification. Classification model 35 is generated using supervised machine learning. To train the classification model 35, training sets and validation sets are generated (collectively referred to as "ML sets"). The ML set are generated by collecting sample evoked responses (e.g., the NF, FF, and DFF potentials of evoked responses) for each classification. Features are extracted or derived from the sample evoked response. These features include quantifiable values, such as the absolute or relative voltages of, for example, the Q-wave, the R-wave, and the S-wave, etc. and the associated timings of these characteristics. Through training, classification model 35 determines the which of the features are physiologically significant features. That is, the physiologically significant features are the features that, through machine learning, the classification model 35 determines are relevant to the classification process. For example, there may be fifteen features that may be extracted and/or derived from the sample evoked responses, but through machine learning, only thirteen of the features may be used to classify evoked responses (e.g., the physiologically significant features). That is, in some examples, the physiologically significant features include some, but not all, of the features of the evoked responses (e.g., the physiologically significant features are a subset of the features of the evoked response, etc.). In such an example, when implemented by IMD 16, pacing analysis circuitry 34 may only need to extract and/or derive the thirteen physiologically significant features instead of all of the possible extractable and/or derivable features. Different machine learning algorithms may be used, such as a classification algorithm (e.g., a decision tree algorithm, a k-nearest neighbor (KNN) algorithm, etc.) or a regression algorithm (e.g., a linear regression algorithm, a polynomial regression algorithm, etc.). In some examples, a classification machine learning algorithm may produce a decision tree model to classify the pacing based on the features of the evoked responses.

Figure 4:
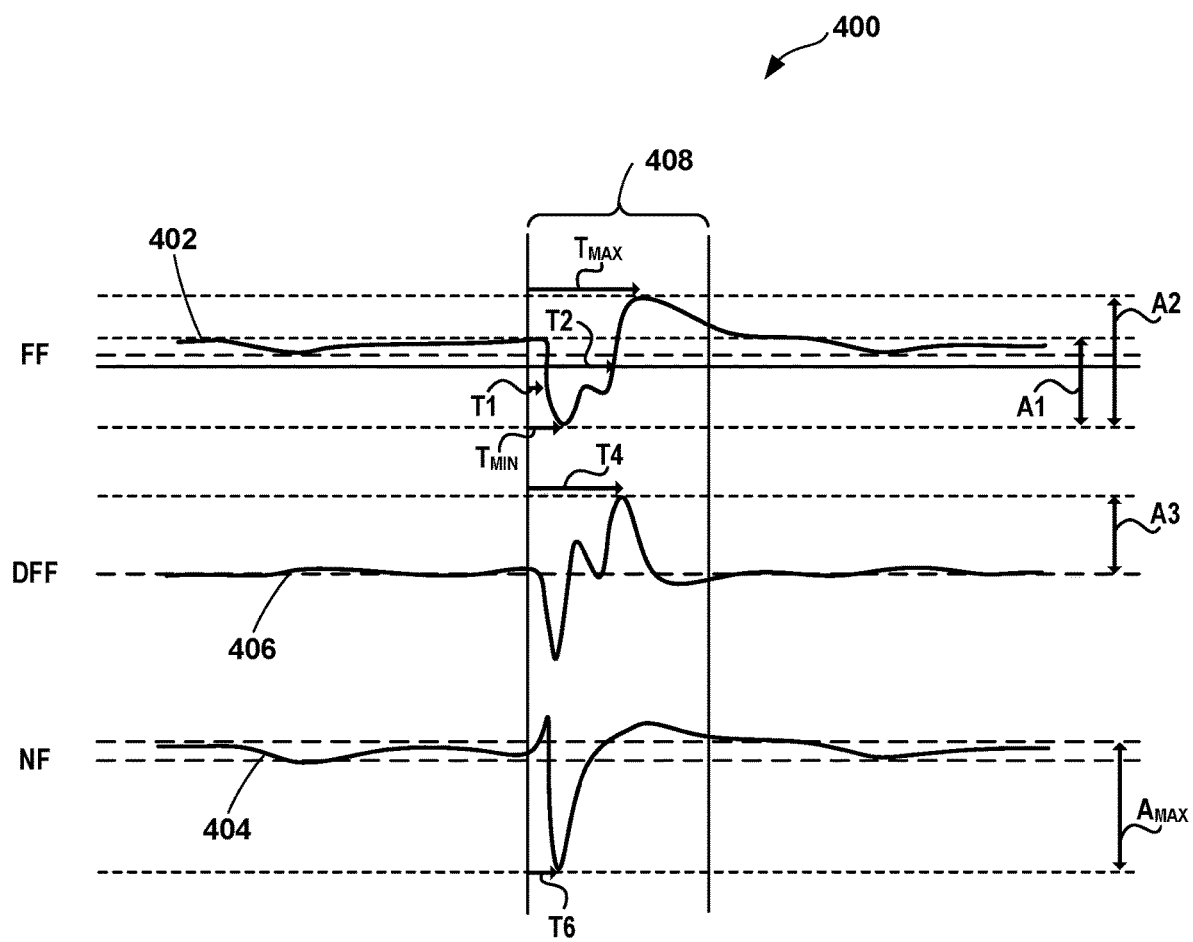
FIG. 4 depicts an example evoked response illustrating physiologically meaningful features that may be extracted from the evoked response and used to classify the evoked response, in accordance with the teachings of this disclosure.

FIG. 4 depicts an example evoked response 400 illustrating physiologically meaningful features that may be extracted from evoked response 400 that may be used to classify evoked response 400. In the illustrated examples, evoked response 400 includes a far filed (FF) potential 402, a near filed (NF) potential 404, and a differential far field (DFF) potential 406. FF potential 402 may be measured between electrode 25A of lead 22 (sometime referred to as "RVtip") and housing electrode 4 (sometimes referred to as "Can"). In some examples that include other electrodes, such as an ICD that includes defibrillation electrodes, FF potential 402 may be measured between electrode 25A and such other electrodes. NF potential 404 may be measured between electrode 25A of lead 22 and electrode 25B of lead 22 (sometime referred to as "RVring"). DFF potential 406 may be a first order differential of the FF potential 402. The physiologically meaningful features may be extracted over window 408 (e.g., 220 milliseconds (ms), etc.) after the pacing is delivered.

FF potential 402, FF potential 404, and DFF potential 406 may have physiologically meaningful features that may be used to classify evoked response 400. The following are a non-exhaustive list of potential physiologically meaningful features that may be used by classification model 35. One physiologically meaningful feature may be a time between the pacing and the response of FF potential 402 when the negative deflection is below a certain threshold (sometimes referred to as "T1", and the zero line is adjusted based on the EGM value before the start of ventricular pacing). One physiologically meaningful feature may be a width, as a measure of time, of the FF potential 402 at negative deflection (e.g., starting and ending when the potential crosses of a pre-defined threshold) (sometimes referred to as "T2"). One physiologically meaningful feature may be a time between the start of ventricular pacing to the positive peak of DFF potential 406 (sometimes referred to as "T4"). One physiologically meaningful feature may be a time between the start of ventricular pacing to the positive peak of NF potential 404 (sometimes referred as "T6"). One physiologically meaningful feature may be a time between the start of ventricular pacing to the positive peak of FF potential 402 (sometimes referred to as "$T_{MAX}$"). One physiologically meaningful feature may be a time between the start of ventricular pacing to the negative peak of FF potential 402 *sometimes referred to as "$T_{MIN}$"). One physiologically meaningful feature may be a negative peak amplitude of FF potential 402 from zero line within window 408 (sometimes referred to as "A1"). One physiologically meaningful feature may be an amplitude of FF potential 402 from negative peak to positive peak within window 408 (sometimes referred to as "A2"). One physiologically meaningful feature may be a positive peak amplitude of DFF potential 406 within a window 408 (sometimes referred to as "A3"). One physiologically meaningful feature may be an absolute peak amplitude from zero line of NF potential 404 (sometimes referred to as "AMAX"). One physiologically meaningful feature may be a negative slope following the maximum positive peak of FF potential 402 (sometimes referred to as "SP1"). Other physiologically meaningful features may be derived, such as a ratio of T4 to A3, etc.

Figure 5A:
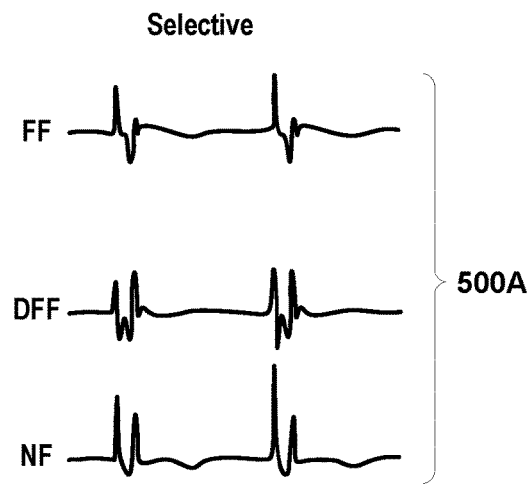
FIGS. 5A, 5B, 5C, and 5D depict example classifications for evoked responses that were classified in accordance with the teachings of this disclosure.
Figure 5B:
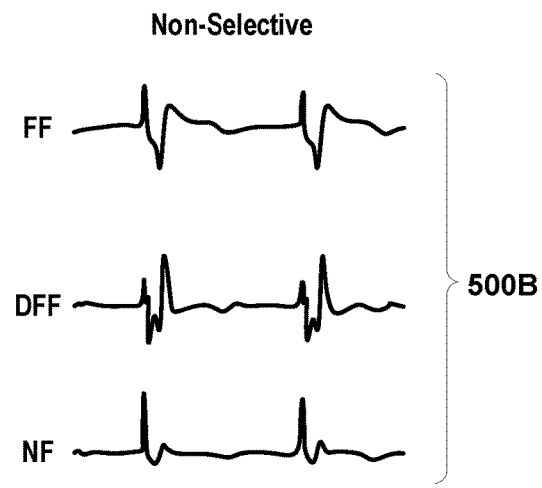
Figure 5C:
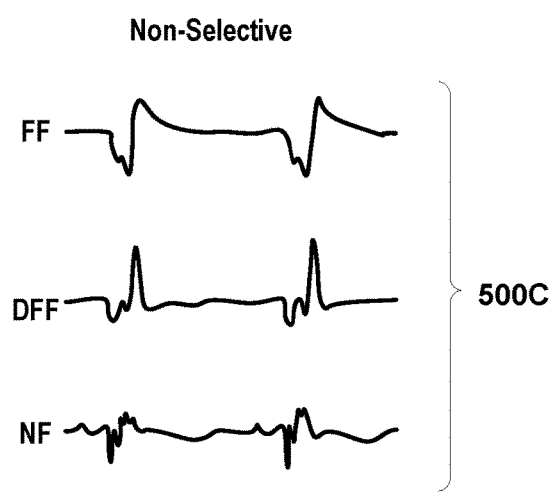
Figure 5D:
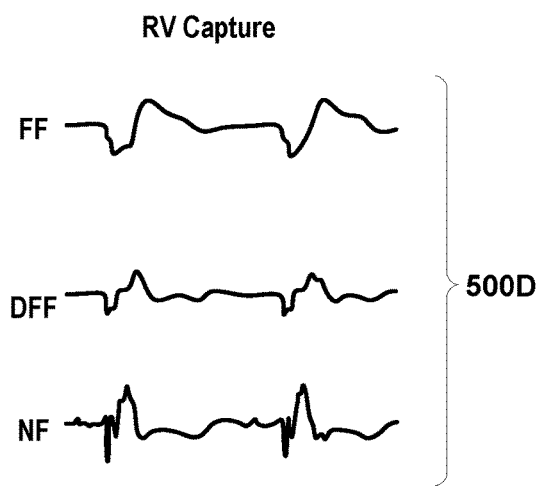

FIGS. 5A, 5B, 5C, and 5D depict example classifications for evoked responses 500A, 500B, 500C, and 500D that were classified in accordance with the teachings of this disclosure. Pacing, as evidenced by the evoked responses, may be categorized as 'selective capture," "non-selective capture," "RV capture," and "no capture" (sometimes referred to a "no ventricular capture"). In some examples, pacing categorized as "RV capture" may further be categorized as "fusion capture" (e.g., multiple electrical impulses act upon the right ventricular chamber) and "right bundle capture" (e.g., capture of just the bundle of Purkinje fibers 30 of right ventricle 28). FIG. 5A illustrates an evoked response 500A indicative of selective capture. FIG. 5B illustrated an evoked response 500B indicative of non-selective capture. FIG. 5C illustrated an evoked response 500C indicative of non-selective capture. FIG. 5D illustrated an evoked response 500D indicative of RV capture.

Figure 6:
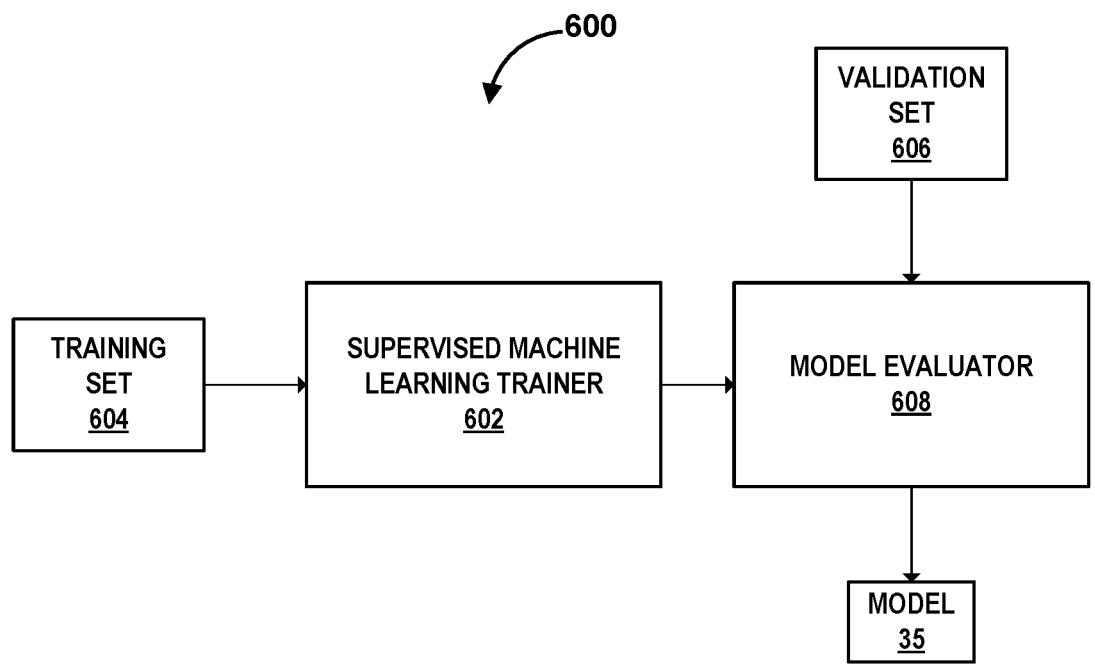
FIG. 6 is a conceptual diagram illustrating an example system to generate the classification model of FIG. 1 using supervised machine learning, in accordance with the teachings of this disclosure.

FIG. 6 is a conceptual diagram illustrating an example system 600 to generate the classification model of FIG. 1 using supervised machine learning, in accordance with the teachings of this disclosure. Supervised machine learning trainer 602 generates a model (e.g., model 35) that may operate on IMD 16 to classify evoked responses (e.g., evoked responses 500A, 500B, 500C, and 500D of FIG. 5). Through supervised machine learning, the machine learning trainer 602 identifies which of the physiologically meaningful features are to be extracted from evoked responses to classify the pacing. Machine learning trainer 602 infers relationships between inputs (e.g., the physiologically meaningful features) and outputs (e.g., the classifications) from a set of labeled pairs. The labeled pairs each include (a) a set of physiologically meaningful features extracted from an evoked response and (b) the classification of that evoked response. The labeled pairs are split into one or more training sets 604 and one or more validation sets 606. Machine learning trainer 602 infers relationships between the physiologically meaningful features and classifications based on the labeled pairs in training set. In some examples, machine learning trainer 602 uses a classification tree algorithm to produce a candidate model. The candidate model is then evaluated by model evaluator 608 using validations sets 606. Model evaluator 608 scores the candidate model based on, for example, a percentage of classifications that were correct (sometimes referred to as "true positives") and a percentage of classifications that were incorrect (sometimes referred to as "false negatives"). Each classification may be scored separately. For example, model evaluator 608 may separately score the "Selective Capture" classification, the "Non-Selective Capture" classification, the "RV Capture" classification, and the "No Capture" classification. A model may be accepted if all classifications satisfy (e.g., are greater than or equal to) a true positive percentage and/or all classifications satisfy (e.g., are less than) a false negative percentage. For example, a candidate model may be accepted if the true positive percentage for all classifications are at least 85 percent and no one classification is falsely identified as another classification more than 5 percent of the time. If a candidate model fails, machine learning trainer 602 may generate a new candidate model with one or more different sets of training data (e.g., labeled pairs may be redistributed randomly between training sets 604 and validation sets 606, etc.) after tuning the parameters of the machine learning algorithm.

Figure 7:
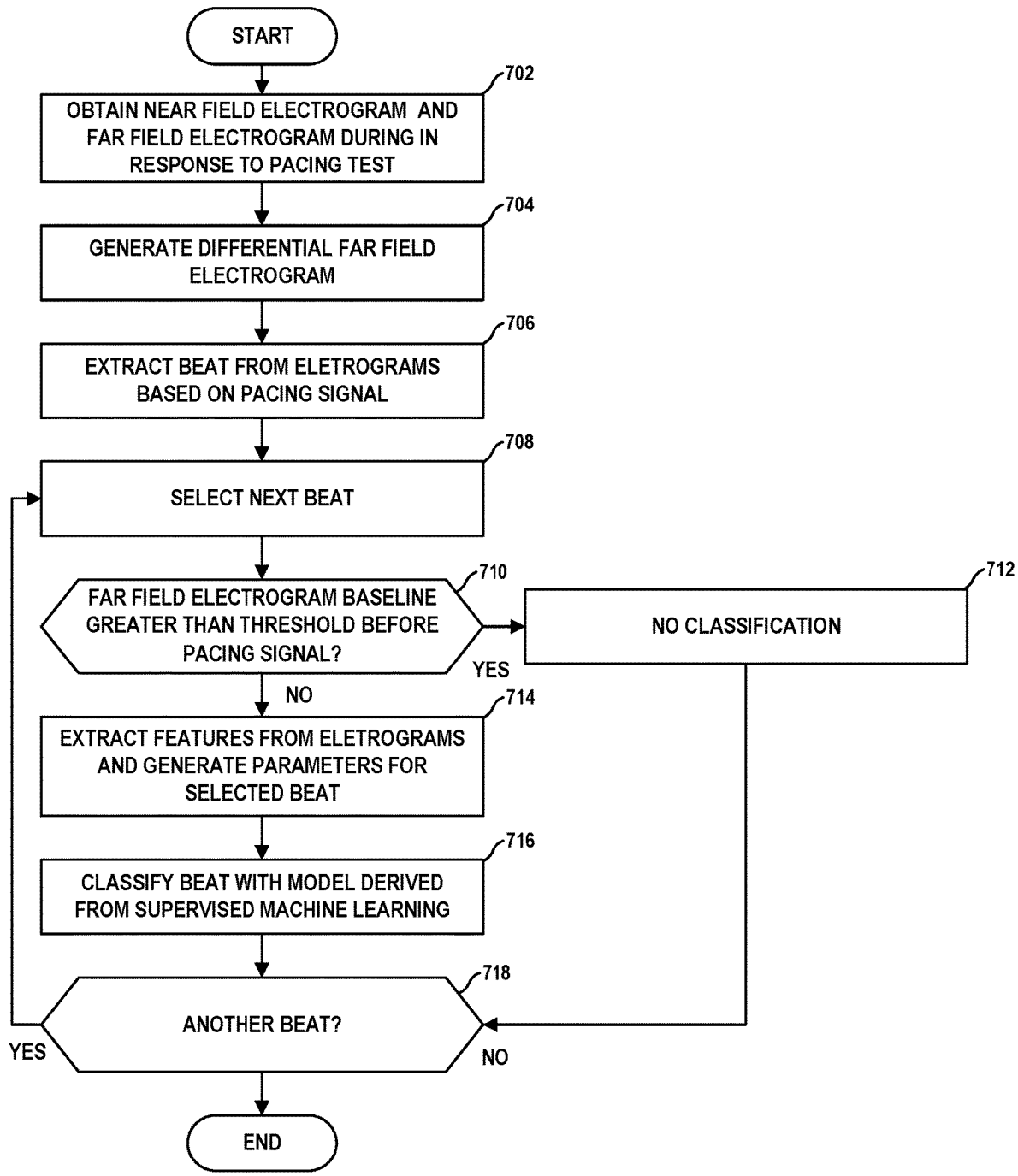
FIG. 7 is a flowchart of an example method to classify evoked responses, in accordance with the teachings of this disclosure.

FIG. 7 is a flowchart of an example method to classify evoked responses, in accordance with the teachings of this disclosure. From time to time, IMD 16 performs a pacing test. For example, IMD 16 may perform a pacing test daily or weekly at a time when patient 14 is likely asleep. IMD 16 uses the pacing test to, for example, determine whether the current stimulation level of pacing is providing effective capture and whether a different amplitude of stimulation (e.g., an amplitude that uses a lower voltage, etc.) may still provide effective capture. Initially, IMD 16 captures a near field (NF) electrogram and a far field (FF) electrogram for a period after pacing (e.g., 100 ms, 160 ms, 220 ms, etc.) (702). IMD 16 generates a differential far field (DIFF) electrogram that is a first order differential of the far field electrogram (704). In some examples, the pacing test may provide a series of pacing such that IMD 16 may extract FF, NF, and DFF potentials for multiple beats. In some such examples, one or more of the finals pacing stimulus signals may change one or more pacing parameters (e.g., amplitude, pulse width, etc.) such that a new pacing parameter may be compared to existing pacing parameters. IMD 16 extracts the beat(s) (706).

IMD 16 selects the first or next beat (708). IMD 16 determines whether an FF electrogram baseline is greater than a threshold (e.g., 0.8 mV, etc.) before the pacing stimulus (710). When the FF electrogram baseline is not greater than a threshold ("NO" at 710) IMD 16 determines that the capture "beat" is an artifact and provides no classification (712). Otherwise, when IMD 16 determines whether a FF electrogram baseline is greater than a threshold ("YES" at 710), IMD 16 extracts features from the FF, NF and DFF electrograms and, in some examples, derive parameters based on features and parameters used by model 35 to classify the beats (e.g., a specific list of features provided when model 35 is downloaded into IMD 16, etc.) (714). IMD 16 classifies the beat using model 35 and the features and parameters (716). When there is another beat to classify ("YES" at 718), IMD 16 selects the next beat (708). When there is not another beat to classify ("NO" at 718), the method ends. In some examples IMD 16 may further take actions in response to the classification, such as adjusting the amplitude and/or pulse width of the stimulation. In some examples, IMD 16 may perform pacing tests with reduced stimulus amplitudes until the beats change from a "selective capture" classification to a "non-selective capture" classification. In some such examples, IMD 16 may set the amplitude of the stimulus based on the lowest amplitude (e.g., with an added safety margin) that was classified as "selective capture."

Figure 8:
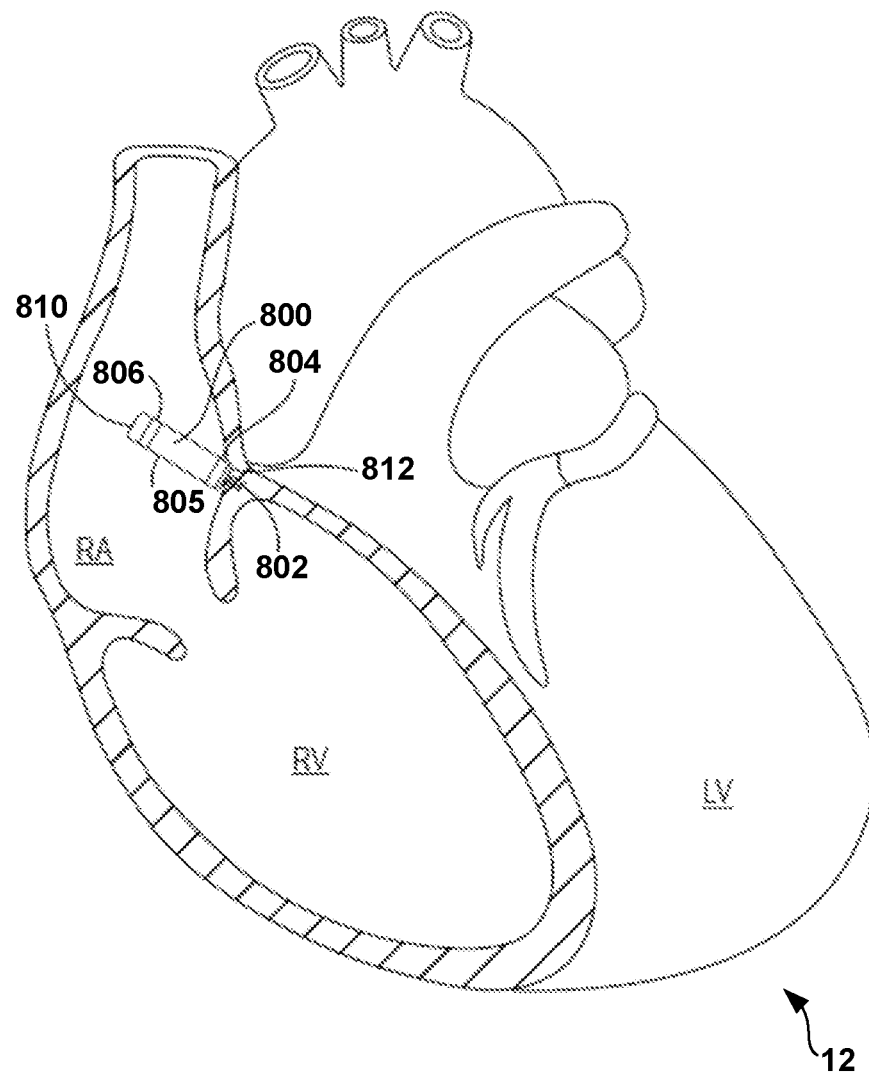
FIG. 8 is a is a conceptual diagram of a leadless intracardiac pacemaker positioned within the right atrium for providing ventricular pacing via the His bundle, in accordance with the teachings of this disclosure.

FIG. 8 is a conceptual diagram of a leadless intracardiac pacemaker 800 positioned within the right atrium (RA) of heart 12 for providing ventricular pacing via the His bundle. Pacemaker 800 may include a distal tip electrode 802 extending away from a distal end 812 of the pacemaker housing 805. Intracardiac pacemaker 800 is shown implanted in the RA of the patient's heart 12 to place distal tip electrode 802 for delivering pacing pulses to the His bundle. For example, the distal tip electrode 802 may be inserted into the inferior end of the interatrial septum, beneath the AV node and near the tricuspid valve annulus to position tip electrode 802 in, along or proximate to the His bundle. Distal tip electrode 102 may be a helical electrode providing fixation to anchor the pacemaker 800 at the implant position. In other examples, pacemaker 800 may include a fixation member that includes one or more tines, hooks, barbs, helices, or other fixation member(s) that anchor the distal end of the pacemaker 800 at the implant site.

A portion of the distal tip electrode 802 may be electrically insulated such that only the most distal end of tip electrode 802, furthest from housing distal end 812, is exposed to provide targeted pacing at a tissue site that includes a portion of the His bundle. One or more housing-based electrodes 804 and 806 may be carried on the surface of the housing of pacemaker 100. Electrodes 804 and 806 are shown as ring electrodes circumscribing the longitudinal sidewall of pacemaker housing 805 extending from distal end 812 to proximal end 810. In other examples, a return anode electrode used in sensing and pacing may be positioned on housing proximal end 810. Pacing of the ventricles, e.g., via the His-Purkinje system, may be achieved using the distal tip electrode 802 as the cathode electrode and either of the housing-based electrodes 804 and 806 as the return anode.

Cardiac electrical signals produced by heart 12 may be sensed by pacemaker 800 using a sensing electrode pair selected from electrodes 802, 804 and 806. For example, a ventricular electrical signal for sensing ventricular R-waves may be sensed using distal tip electrode 812 and distal housing-based electrode 804. An atrial electrical signal for sensing atrial P-waves may be sensed using electrodes 804 and 806. The atrial and ventricular electrical signals may be analyzed for sensing atrial and ventricular events. In some examples, pacemaker 800 is a dual chamber pacemaker configured to deliver atrial pacing pulses using a housing based distal electrode 804 and proximal electrode 806 and deliver ventricular pacing pulses via tip electrode 802 and proximal electrode 806. Examples of dual chamber intracardiac pacemakers which may incorporate the techniques disclosed herein for controlling ventricular sensing parameters are generally disclosed in U.S. Patent Application Publication No. 2019/0083800 (Yang, et al.), incorporated herein by reference in its entirety.

Processing circuitry of pacemaker 800 includes pacing analysis circuitry (e.g., pacing analysis circuitry 34, etc.) and a classification model (e.g., classification model 35, etc.) configured to classifying evoked responses resulting from pacing. From time to time, shortly after delivering the electrical stimulation (e.g., within 90 to 120 milliseconds, etc.), the pacing signal analysis circuitry measures an evoked response of the heart muscle of heart 12. The evoked response is measured via an EGM sensed via one or more electrodes of pacemaker 800. The cardiac signal analysis circuitry may measure the FF potential and the NF potential. The cardiac signal analysis circuitry may also determine the DFF potential. The cardiac EGM that includes an evoked response may include the P-waves, the R-waves, and the T-waves. As described above, the cardiac EGM of an evoked response may include physiologically meaningful features. These physiologically meaningful features are extracted by pacing analysis circuitry. Pacing analysis circuitry then uses classification model to classify the evoked response. In some examples, pacemaker 800 may take actions based on the classification of the evoked response, such as adjusting pacing parameters and/or providing an alert (e.g., to external device 24).

The following examples are described herein.

Example 1A. A system comprises stimulation circuitry configured to generate a pacing stimulus, sensing circuitry configured to sense an evoked response after the pacing stimulus, and processing circuitry configured to: determine classification features from the evoked response, apply the classification features to a classification model, the classification model generated by a machine learning algorithm using one or more test sets comprising a plurality of sample evoked responses for each of a plurality of classifications, and based on the output of the model, classify the evoke response as one of the plurality of classifications.

Example 1B. The system of Example 1A, wherein the classification features are a subset of possible features of the evoked response.

Example 1C. The system of 1B, wherein the classification features are determined by the machine learning algorithm from the possible features of the evoked response.

Example 1D. The system of any of Examples 1A or 1B, wherein the evoked response is indicative of capture of heart muscle in response to the pacing stimulus, and wherein the plurality of classifications includes selective capture, non-selective capture, right ventricular capture, and no ventricular capture Example 1E. The system of any of Examples 1A, 1B, or 1D, wherein the classification model is a decision tree model.

Example 1F. The system of any of Examples 1A, 1B, 1D, or 1E, wherein the processing circuitry is configured to, in response to classifying the evoked response as one of the plurality of classifications, generate an alert.

Example 1G. The system of any of Examples 1A, 1B, 1D, 1E, or 1F, wherein the processing circuitry is configured to, in response to classifying the evoked response as one of the plurality of classifications, change a voltage level of pacing stimulus.

Example 1H. The system of any of Examples 1A, 1B, 1D, 1E, 1F, or 1G, including an implantable medical device comprising the stimulation circuitry, the sensing circuitry, and the processing circuitry.

Example 1I. The system of any of Examples 1A, 1B, 1D, 1E, 1F, 1G, or 1H, wherein the sensing circuitry is configured to sense a near field electrogram (EGM) of the evoked response and a far-field EGM of the evoked response, and wherein the processing circuitry is configured to determine a differential far field EMG.

Example 1J. The system of Examples 1I, wherein the classification features comprise two or more of (a) a time (T1) between the pacing stimulus and a response of the FF potential when a negative deflection is below a predefined threshold, (b) a width (T2) of the FF potential at the negative deflection, (c) a time (T4) between a start of the pacing stimulus to a positive peak of the DFF potential, (d) a time (T6) between the start of the pacing stimulus to a positive peak of the NF potential, (e) a time (TMAX) between the start of the pacing stimulus to a positive peak of the FF potential, (f) a time (TMIN) between the start of ventricular pacing to a negative peak of the FF potential, (g) a negative peak amplitude (A1) of the FF potential from a zero line within a predefined window, (h) an amplitude (A2) of the FF potential from the negative peak to a positive peak within the predefined window 408, (i) a positive peak amplitude (A3) of the DFF potential within the predefined window, (j) an absolute peak amplitude (AMAX) from a zero line of the NF potential, and (k) a negative slope (SP1) following a maximum positive peak of the FF potential.

Example 2A. A method comprising generating, by stimulation circuitry, a pacing stimulus, sensing, by sensing circuitry, an evoked response after the pacing stimulus, determining, by processing circuitry, classification features from the evoked response, applying, by the processing circuitry, the classification features to a classification model, the classification model generated by a machine learning algorithm using one or more test sets comprising a plurality of sample evoked responses for each of a plurality of classifications, and based on the output of the model, classifying, by the processing circuitry, the evoke response as one of the plurality of classifications.

Example 2B. The method of Example 2A, wherein the classification features are a subset of possible features of the evoked response.

Example 2C. The method of Example 2B, wherein the classification features are determined by the machine learning algorithm from the possible features of the evoked response.

Example 2D. The method of any of Examples 2A or 2B, wherein the evoked response is indicative of capture of heart muscle in response to the pacing stimulus, and wherein the plurality of classifications includes selective capture, non-selective capture, right ventricular capture, and no ventricular capture.

Example 2E. The method of any of Examples 2A, 2B or 2D, wherein the classification model is a decision tree model.

Example 2F. The method of any of Examples 2A, 2B, 2D, or 2E, comprising, in response to classifying the evoked response as one of the plurality of classifications, generating an alert.

Example 2G. The method of any of Examples 2A, 2B, 2D, 2E, or 2F, comprising, in response to classifying the evoked response as one of the plurality of classifications, changing a voltage level of pacing stimulus.

Example 2H. The method of any of Examples 2A, 2B, 2D, 2E, 2F, and 2G, wherein the stimulation circuitry, the sensing circuitry, and the processing circuitry are within an implantable medical device.

Example 2I. The method of any of Examples 2A, 2B, 2D, 2E, 2F, 2G, and 2H, wherein the evoked response includes a far field (FF) potential, a near field (NF) potential and a differential far field (DFF) potential, and wherein the classification features comprise two or more of (a) a time (T1) between the pacing stimulus and a response of the FF potential when a negative deflection is below a predefined threshold, (b) a width (T2) of the FF potential at the negative deflection, (c) a time (T4) between a start of the pacing stimulus to a positive peak of the DFF potential, (d) a time (T6) between the start of the pacing stimulus to a positive peak of the NF potential, (e) a time (TMAX) between the start of the pacing stimulus to a positive peak of the FF potential, (f) a time (TMIN) between the start of ventricular pacing to a negative peak of the FF potential, (g) a negative peak amplitude (A1) of the FF potential from a zero line within a predefined window, (h) an amplitude (A2) of the FF potential from the negative peak to a positive peak within the predefined window 408, (i) a positive peak amplitude (A3) of the DFF potential within the predefined window, (j) an absolute peak amplitude (AMAX) from a zero line of the NF potential, and (k) a negative slope (SP1) following a maximum positive peak of the FF potential.

Example 2J. The method of any of Examples 2A, 2B, 2D, 2E, 2F, 2G, or 2H, wherein sensing the evoke response includes sensing a near field electrogram (EGM) of the evoked response and a far-field EGM of the evoked response, the method comprising determining, by the processing circuitry, a differential far field EMG based on the far field EMG.

Example 3A. A computer readable medium comprising instructions, that when executed, cause an implantable medical device (IMD) to: generate, by stimulation circuitry of the IMD, a pacing stimulus; sense, by sensing circuitry of the IMD, an evoked response after the pacing stimulus; determine, by processing circuitry of the IMD, classification features from the evoked response; apply, by the processing circuitry, the classification features to a classification model, the classification model generated by a machine learning algorithm using one or more test sets comprising a plurality of sample evoked responses for each of a plurality of classifications; and based on the output of the model, classify, by the processing circuitry, the evoke response as one of the plurality of classifications.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system comprising:
    stimulation circuitry configured to generate a pacing stimulus;
    sensing circuitry configured to sense an evoked response after the pacing stimulus, wherein the evoked response is indicative of capture of heart muscle in response to the pacing stimulus; and
    processing circuitry configured to:
       determine classification features from the evoked response;
       apply the classification features to a classification model, the classification model generated by a machine learning algorithm using one or more test sets comprising a plurality of sample evoked responses for each of a plurality of classifications, wherein the plurality of classifications includes a selective capture, non-selective capture, and right ventricular capture;
       based on the output of the model, classify the evoke response as a non-selective capture classification as a change from a selective capture classification for a previous evoked response; and
       in response to determining the evoked response includes the change from the selective capture classification to the non-selective capture classification, change an amplitude level of pacing stimulus based on an amplitude level of the pacing stimulus causing an evoked response including a selective capture classification.

2. The system of claim 1, wherein the classification features are a subset of possible features of the evoked response.

3. The system of claim 2, wherein the classification features are determined by the machine learning algorithm from the possible features of the evoked response.

4. The system of claim 1, wherein the classification model is a decision tree model.

5. The system of claim 1, wherein the processing circuitry is further configured to, in response to classifying the evoked response as one of the plurality of classifications, generate an alert.

6. The system of claim 1, wherein the processing circuitry is configured to, in response to determining the evoked response includes the change from the selective capture classification to the non-selective capture classification, change the amplitude level by changing a voltage level of the pacing stimulus.

7. The system of claim 1, including an implantable medical device comprising the stimulation circuitry, the sensing circuitry, and the processing circuitry.

8. The system of claim 1, wherein the sensing circuitry is configured to sense a near field (NF) electrogram (EGM) of the evoked response and a far-field (FF) EGM of the evoked response, and wherein the processing circuitry is configured to determine a differential far field (DFF) EGM.

9. The system of claim 8, wherein the classification features comprise two or more of (a) a time (T1) between the pacing stimulus and a response of the FF potential when a negative deflection is below a predefined threshold, (b) a width (T2) of the FF potential at the negative deflection, (c) a time (T4) between a start of the pacing stimulus to a positive peak of the DFF potential, (d) a time (T6) between the start of the pacing stimulus to a positive peak of the NF potential, (e) a time (TMAX) between the start of the pacing stimulus to a positive peak of the FF potential, (f) a time (TMIN) between the start of ventricular pacing to a negative peak of the FF potential, (g) a negative peak amplitude (A1) of the FF potential from a zero line within a predefined window, (h) an amplitude (A2) of the FF potential from the negative peak to a positive peak within the predefined window 408, (i) a positive peak amplitude (A3) of the DFF potential within the predefined window, (j) an absolute peak amplitude (AMAX) from a zero line of the NF potential, and (k) a negative slope (SP1) following a maximum positive peak of the FF potential.

10. A method comprising:
generating, by stimulation circuitry, a pacing stimulus;
sensing, by sensing circuitry, an evoked response after the pacing stimulus, wherein the evoked response is indicative of capture of heart muscle in response to the pacing stimulus;
determining, by processing circuitry, classification features from the evoked response;
applying, by the processing circuitry, the classification features to a classification model, the classification model generated by a machine learning algorithm using one or more test sets comprising a plurality of sample evoked responses for each of a plurality of classifications, wherein the plurality of classifications includes a selective capture, non-selective capture, and right ventricular capture;
based on output of the model, classifying, by the processing circuitry, the evoked response as a non-selective capture classification as a change from a selective capture classification for a previous evoked response; and
in response to determining the evoked response includes the change from the selective capture classification to the non-selective capture classification, changing an amplitude level of pacing stimulus based on an amplitude level of the pacing stimulus causing an evoked response including a selective capture classification.

11. The method of claim 10, wherein the classification features are a subset of possible features of the evoked response.

12. The method of claim 11, wherein the classification features are determined by the machine learning algorithm from the possible features of the evoked response.

13. The method of claim 10, wherein the classification model is a decision tree model.

14. The method of claim 10, comprising, in response to determining the evoked response includes the change from the selective capture classification to the non-selective capture classification, changing the amplitude level by changing a voltage level of the pacing stimulus.

15. The method of claim 10, wherein the stimulation circuitry, the sensing circuitry, and the processing circuitry are within an implantable medical device.

16. The method of claim 10, wherein the evoked response includes a far field (FF) potential, a near field (NF) potential and a differential far field (DFF) potential, and wherein the classification features comprise two or more of (a) a time (T1) between the pacing stimulus and a response of the FF potential when a negative deflection is below a predefined threshold, (b) a width (T2) of the FF potential at the negative deflection, (c) a time (T4) between a start of the pacing stimulus to a positive peak of the DFF potential, (d) a time (T6) between the start of the pacing stimulus to a positive peak of the NF potential, (e) a time (TMAX) between the start of the pacing stimulus to a positive peak of the FF potential, (f) a time (TMIN) between the start of ventricular pacing to a negative peak of the FF potential, (g) a negative peak amplitude (A1) of the FF potential from a zero line within a predefined window, (h) an amplitude (A2) of the FF potential from the negative peak to a positive peak within the predefined window, (i) a positive peak amplitude (A3) of the DFF potential within the predefined window, (j) an absolute peak amplitude (AMAX) from a zero line of the NF potential, and (k) a negative slope (SP1) following a maximum positive peak of the FF potential.

17. The method of claim 10, wherein sensing the evoke response includes sensing a near field electrogram (EGM) of the evoked response and a far-field EGM of the evoked response, the method comprising determining, by the processing circuitry, a differential far field EGM based on the far field EGM.

18. A non-transitory computer readable medium comprising instructions, that when executed, cause an implantable medical device (IMD) to:
generate, by stimulation circuitry of the IMD, a pacing stimulus;
sense, by sensing circuitry of the IMD, an evoked response after the pacing stimulus, wherein the evoked response is indicative of capture of heart muscle in response to the pacing stimulus;
determine, by processing circuitry of the IMD, classification features from the evoked response;
apply, by the processing circuitry, the classification features to a classification model, the classification model generated by a machine learning algorithm using one or more text sets comprising a plurality of sample evoked responses for each of a plurality of classifications, wherein the plurality of classifications includes a selective capture, non-selective capture, and right ventricular capture;
based on output of the model, classify, by the processing circuitry, the evoked response as a non-selective capture classification as a change from a selective capture classification for a previous evoked response; and
in response to determining the evoked response includes the change from the selective capture classification to the non-selective capture classification, change an amplitude level of pacing stimulus base on an amplitude level of the pacing stimulus causing an evoked response including a selective capture classification.

19. The system of claim 1, wherein to change the amplitude level of the pacing stimulus based on the amplitude level of the pacing stimulus having the evoked response including the selective capture classification, the processing circuitry is configured to:

change the amplitude level of pacing stimulus based on a lowest amplitude level of the pacing stimulus causing the evoked response including the selective capture classification.

\* \* \* \* \*